(12) United States Patent
Grant et al.

(10) Patent No.: US 11,597,102 B2
(45) Date of Patent: Mar. 7, 2023

(54) GEAR PACKAGING FOR ROBOTIC JOINTS

(71) Applicant: CMR SURGICAL LIMITED, Cambridge (GB)

(72) Inventors: James Oliver Grant, Histon (GB); Keith Marshall, Great Abington (GB); Thomas Bates Jackson, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 327 days.

(21) Appl. No.: 15/655,310

(22) Filed: Jul. 20, 2017

(65) Prior Publication Data
US 2018/0021960 A1 Jan. 25, 2018

(30) Foreign Application Priority Data

Jul. 22, 2016 (GB) ...................................... 1612763

(51) Int. Cl.
*B25J 17/02* (2006.01)
*B25J 9/10* (2006.01)
*A61B 34/30* (2016.01)

(52) U.S. Cl.
CPC ........... *B25J 17/0283* (2013.01); *A61B 34/30* (2016.02); *B25J 9/102* (2013.01); *A61B 2034/306* (2016.02)

(58) Field of Classification Search
CPC ....... A61B 34/30; B25J 17/02; B25J 17/0258; B25J 17/0283; F16H 55/17; F16H 55/20; F16H 1/145; F16H 37/065
(Continued)

(56) References Cited

U.S. PATENT DOCUMENTS

| 1,822,846 | A | * | 9/1931 | Wildhaber | ............ B23F 19/025 |
|---|---|---|---|---|---|
| | | | | | 451/47 |
| 2,908,187 | A | * | 10/1959 | Saari | ...................... F16D 11/10 |
| | | | | | 74/665 K |

(Continued)

FOREIGN PATENT DOCUMENTS

| DE | 3736355 A1 | 10/1987 |
|---|---|---|
| DE | 3736355 A1 | 5/1988 |

(Continued)

OTHER PUBLICATIONS

Collins, Danielle. "Hypoid Gearboxes: What are they and where are they used?". Oct. 18, 2017. https://www.motioncontroltips.com/hypoid-gearboxes-what-are-they-and-where-are-they-used/. Retrieved from the internet: Jul. 20, 2020. (Year: 2017).*

(Continued)

*Primary Examiner* — William C Joyce
*Assistant Examiner* — T. Scott Fix
(74) *Attorney, Agent, or Firm* — Renner, Otto, Boisselle & Sklar, LLP

(57) ABSTRACT

A robot arm comprising a first arm segment and a second arm segment coupled to each other by a first revolute joint having a first rotation axis and a second revolute joint having a second rotation axis non-parallel to the first rotation axis, and a joint mechanism for articulating the first arm segment relative to the second arm segment about the first and second rotation axes, the joint mechanism comprising: a first driven gear disposed about an axle coincident with the first rotation axis, the axle being fast with a first arm segment of the robot arm; a second driven gear disposed about the second rotation axis and fast with a second arm segment of the robot arm and fast with the first driven gear about the first rotation axis; a first drive gear configured to drive the first driven gear to rotate about the axle, the first drive gear being arranged to engage the first driven gear; a second drive gear for driving (Continued)

the second driven gear to rotate about the second rotation axis; and an intermediary gear arrangement arranged to engage the second drive gear and the second driven gear and being disposed about the first rotation axis, whereby rotation of the intermediary gear arrangement relative to the first arm segment about the first rotation axis can be driven.

20 Claims, 6 Drawing Sheets

(58) Field of Classification Search
USPC .................. 74/490.03, 435, 459.5; 901/29
See application file for complete search history.

(56) References Cited

U.S. PATENT DOCUMENTS

| | | | | |
|---|---|---|---|---|
| 2,911,167 A * | 11/1959 | Null | G01S 3/786 | 244/3.16 |
| 2,942,491 A * | 6/1960 | Wildhaber | F16H 1/145 | 74/459.5 |
| 2,954,704 A * | 10/1960 | Saari | F16H 55/0853 | 74/466 |
| 2,961,888 A * | 11/1960 | Wildhaber | F16H 55/0853 | 74/459.5 |
| 3,261,223 A * | 7/1966 | Vertut | B25J 9/104 | 74/380 |
| 3,478,620 A * | 11/1969 | Shimanckas | B63H 20/00 | 74/665 GB |
| 3,592,283 A * | 7/1971 | Fischbach | B62D 11/12 | 180/9.44 |
| 3,904,234 A * | 9/1975 | Hill | B25J 15/04 | 250/231.1 |
| 4,307,797 A * | 12/1981 | Belansky | F16D 1/033 | 192/108 |
| 4,480,495 A * | 11/1984 | Obama | B25J 9/06 | 403/54 |
| 4,492,510 A * | 1/1985 | Tanii | B25J 9/1025 | 414/733 |
| 4,499,790 A * | 2/1985 | Helms | B25J 17/0258 | 414/4 |
| 4,501,522 A * | 2/1985 | Causer | B25J 3/04 | 414/4 |
| 4,607,538 A * | 8/1986 | Geisthoff | F16H 7/023 | 474/148 |
| 4,612,996 A * | 9/1986 | Wolf | A01B 69/007 | 104/165 |
| 4,637,773 A * | 1/1987 | Nakashima | B25J 9/1045 | 414/7 |
| 4,761,114 A * | 8/1988 | Barland | B25J 17/0283 | 414/735 |
| 4,961,353 A * | 10/1990 | Okada | B21K 1/30 | 74/434 |
| 4,972,735 A * | 11/1990 | Torii | B25J 17/0283 | 74/665 M |
| 5,079,877 A * | 1/1992 | Abysov | B23F 19/025 | 451/114 |
| 5,116,173 A * | 5/1992 | Goldrich | B23F 9/025 | 409/13 |
| 5,353,659 A * | 10/1994 | Chudy | F16H 19/08 | 74/88 |
| 5,924,330 A * | 7/1999 | Danielsson | B25J 9/103 | 74/490.06 |
| 5,950,502 A * | 9/1999 | Genovese | B41F 13/008 | 74/417 |
| 5,967,580 A * | 10/1999 | Rosheim | B25J 3/04 | 294/106 |
| 6,424,886 B1 * | 7/2002 | Iversen | A61F 2/585 | 700/254 |
| 6,626,059 B1 * | 9/2003 | Fischer | B64C 27/14 | 74/417 |
| 6,871,563 B2 * | 3/2005 | Choset | B25J 9/102 | 74/490.01 |
| 7,734,375 B2 * | 6/2010 | Buehler | B25J 9/102 | 700/245 |
| 7,926,377 B2 * | 4/2011 | Larsson | B25J 9/103 | 901/29 |
| 8,380,351 B2 * | 2/2013 | Okuda | B25J 9/102 | 700/255 |
| 8,414,043 B2 * | 4/2013 | Albin | B25J 15/0213 | 294/106 |
| 8,616,088 B2 * | 12/2013 | Teng | B25J 9/102 | 74/490.05 |
| 8,663,060 B2 * | 3/2014 | Cline | F16H 37/06 | 475/243 |
| 8,967,012 B2 * | 3/2015 | Napau | F16H 55/082 | 74/457 |
| 2003/0036748 A1 * | 2/2003 | Cooper | A61B 17/00234 | 606/1 |
| 2005/0274216 A1 * | 12/2005 | Fleytman | F16H 1/14 | 74/457 |
| 2008/0034920 A1 * | 2/2008 | Inoue | B25J 9/104 | 74/665 M |
| 2010/0095800 A1 * | 4/2010 | Palau | B25J 9/042 | 74/490.03 |
| 2013/0055842 A1 * | 3/2013 | Okada | B25J 9/102 | 74/490.03 |
| 2013/0116706 A1 * | 5/2013 | Lee | A61B 34/30 | 606/130 |
| 2013/0192420 A1 * | 8/2013 | Isobe | F16H 21/54 | 74/99 R |
| 2014/0137691 A1 * | 5/2014 | Nogami | B25J 17/02 | 74/490.06 |
| 2014/0224046 A1 * | 8/2014 | Isobe | B25J 9/0048 | 74/89.14 |
| 2014/0318298 A1 * | 10/2014 | Inoue | B25J 17/02 | 74/490.03 |
| 2016/0361784 A1 * | 12/2016 | Moehlau | B21K 1/305 | |
| 2017/0014197 A1 * | 1/2017 | McCrea | B25J 15/0226 | |
| 2019/0321119 A1 | 10/2019 | Yeung et al. | | |

FOREIGN PATENT DOCUMENTS

| | | | | |
|---|---|---|---|---|
| EP | 0128544 A1 * | 12/1984 | | B25J 17/0258 |
| EP | 0128544 A1 | 12/1984 | | |
| EP | 0148054 A1 | 12/1984 | | |
| EP | 0269751 A1 | 6/1988 | | |
| GB | 2531994 B | 6/2020 | | |
| JP | S59227395 S | 12/1984 | | |
| JP | 1988109994 | 5/1988 | | |
| JP | S63109994 A | 5/1988 | | |
| JP | 2008044019 | 2/2008 | | |
| JP | 2010240834 A | 10/2010 | | |
| JP | 2011026826 | 2/2011 | | |
| JP | 2015085451 A | 5/2015 | | |
| WO | WO 2015/088655 | 6/2015 | | |
| WO | WO 2016/059369 A1 | 4/2016 | | |
| WO | WO 2016/059369 A4 | 4/2016 | | |
| WO | WO-2016071674 A1 * | 5/2016 | | A61B 34/30 |

OTHER PUBLICATIONS

Search Report for GB PCT/GB2017/052121.
Search Report for GB 1612763.1.
First Office Action dated Sep. 1, 2021, for related Chinese Patent Application No. 201780045091.2.
Decision to Grant dated Apr. 22, 2022 in corresponding Japanese Application No. 2019-503254.
Notice for Reasons for Refusal for corresponding Japanese Patent Application No. 2019-503254 dated Jun. 1, 2021.

* cited by examiner

GEAR PACKAGING FOR ROBOTIC JOINTS

BACKGROUND

This disclosure relates to drive arrangements for robot joints. In particular, some embodiments relate to drive arrangements within robotic wrists.

Robots that are required to manipulate objects, which may for example be industrial or surgical robots, frequently have an arm composed of rigid elements which are linked together in series by a number of flexible joints. The joints could be of any type but are typically revolute joints, or a combination of revolute and prismatic joints. The arm extends from a base, whose location might be fixed or moveable, and terminates in a tool or an attachment for a tool. The tool could, for example be a gripping, cutting, illuminating, irradiating or imaging tool. The final joint in the arm may be termed the wrist. The wrist may permit motion about only a single axis, or it may be a complex or compound articulation, which permits rotation about multiple axes.

In the case of a surgical robot there are a number of important criteria that influence the design of the distal joint(s) of the arm.

1. It is desirable for the arm, and particularly its distal portion where the wrist is located, to be small in size. That allows multiple such robot arms to work in close proximity and hence opens up a wider range of surgical procedures that the arm can perform.

2. It is desirable for the joints to be capable of delivering a high torque, so that they can carry heavier tools and deliver high acceleration to the tool tip.

3. It is desirable for all articulations to have position and force/torque sensors, so that the control mechanism can take data from those sensors and for those sensors to take accurate readings.

4. It is desirable for the distal portion of the robot arm to be as light as possible, to reduce the force that must be exerted by more proximal joints of the robot arm.

5. It is desirable for the motion about the joints to be smooth. This leads to improved control of the motion and may be particularly important when a high degree of positional control is required, such as during a surgical procedure.

6. It is desirable for the distal portion of the robot arm to be as light as possible, to reduce the force that must be exerted by more proximal joints of the robot arm.

The number of important criteria makes it difficult to design an arm that best balances all the requirements.

One particular problem is how to fit the motors and gearing into the wrist of a robot arm. The arrangement should be compact but also allow for high stiffness and torque transfer. Many existing designs compromise one of these criteria.

There is a need for an improved drive arrangement for a joint of a robot arm.

SUMMARY

According to a first aspect of the present disclosure there is provided a robot arm comprising a first arm segment and a second arm segment coupled to each other by a first revolute joint having a first rotation axis and a second revolute joint having a second rotation axis non-parallel to the first rotation axis, and a joint mechanism for articulating the first arm segment relative to the second arm segment about the first and second rotation axes, the joint mechanism comprising: a first driven gear disposed about an axle coincident with the first rotation axis, the axle being fast with a first arm segment of the robot arm; a second driven gear disposed about the second rotation axis and fast with a second arm segment of the robot arm and fast with the first driven gear about the first rotation axis; a first drive gear configured to drive the first driven gear to rotate about the axle, the first drive gear being arranged to engage the first driven gear; a second drive gear for driving the second driven gear to rotate about the second rotation axis; and an intermediary gear arrangement arranged to engage the second drive gear and the second driven gear and being disposed about the first rotation axis, whereby rotation of the intermediary gear arrangement relative to the first arm segment about the first rotation axis can be driven.

The first rotation axis may be transverse to the second rotation axis.

The first rotation axis may intersect the second rotation axis.

The first drive gear may be attached to a first drive shaft extending along the first arm segment.

The second drive gear may be attached to a second drive shaft extending along the first arm segment.

The first and second drive shafts may lie on one side of a plane on which the axle lies.

The first driven gear may be a ring gear.

The first driven gear may be a hypoid gear.

The intermediary gear arrangement may be mounted on the axle, the axle being mounted at each of its ends to the first arm segment.

The intermediary gear arrangement may comprise a first intermediate gear arranged to engage the second drive gear; and a second intermediate gear arranged to engage the second driven gear.

The first intermediate gear may be fast with the second intermediate gear.

At least one of the first driven gear and first intermediate gear may be a sector. Only the first driven gear may be a sector.

The operative arc of the sector may be less than or equal to 50 degrees.

The first intermediate gear may be a ring gear.

The first intermediate gear may be a hypoid gear.

The first drive gear and first driven gear may form a first hypoid gear set, and the second drive gear and first intermediate gear form a second hypoid gear set, the first and second hypoid gear sets having an equal skew offset.

The second intermediate gear and the second driven gear may be bevel gears

The second intermediate gear and the second driven gear may be mitre gears.

The joint mechanism may further comprise a carrier attached to the first arm segment by the first revolute joint and attached to the second arm segment by the second revolute joint, the carrier being fast with the first driven gear.

The first and second revolute joints may be wrist joints of the robotic arm.

The robot arm may be a surgical robot arm.

The robot arm may comprise a tool or tool attachment fast with the second arm segment about the first and second rotation axes.

The robot arm may further comprise a third arm segment adjacent the second arm segment and located on the opposite side of the second arm segment to the joint mechanism, and a third revolute joint that attaches the third arm segment to the second arm segment, wherein the third arm segment comprises a tool or a tool attachment.

The robot arm may further comprise a control unit arranged to respond to command signals commanding motion of the robot arm by driving the first and second drive shafts to rotate, the control unit being configured to, when the robot arm is commanded to articulate about the first axis without articulating about the second axis, drive the first shaft to rotate to cause articulation about the first axis and also drive the second shaft to rotate in such a way as to negate parasitic articulation about the second axis.

BRIEF DESCRIPTION OF DRAWINGS

The present disclosure will now be described by way of example with reference to the accompanying drawings. In the drawings.

DETAILED DESCRIPTION

Figure 1:
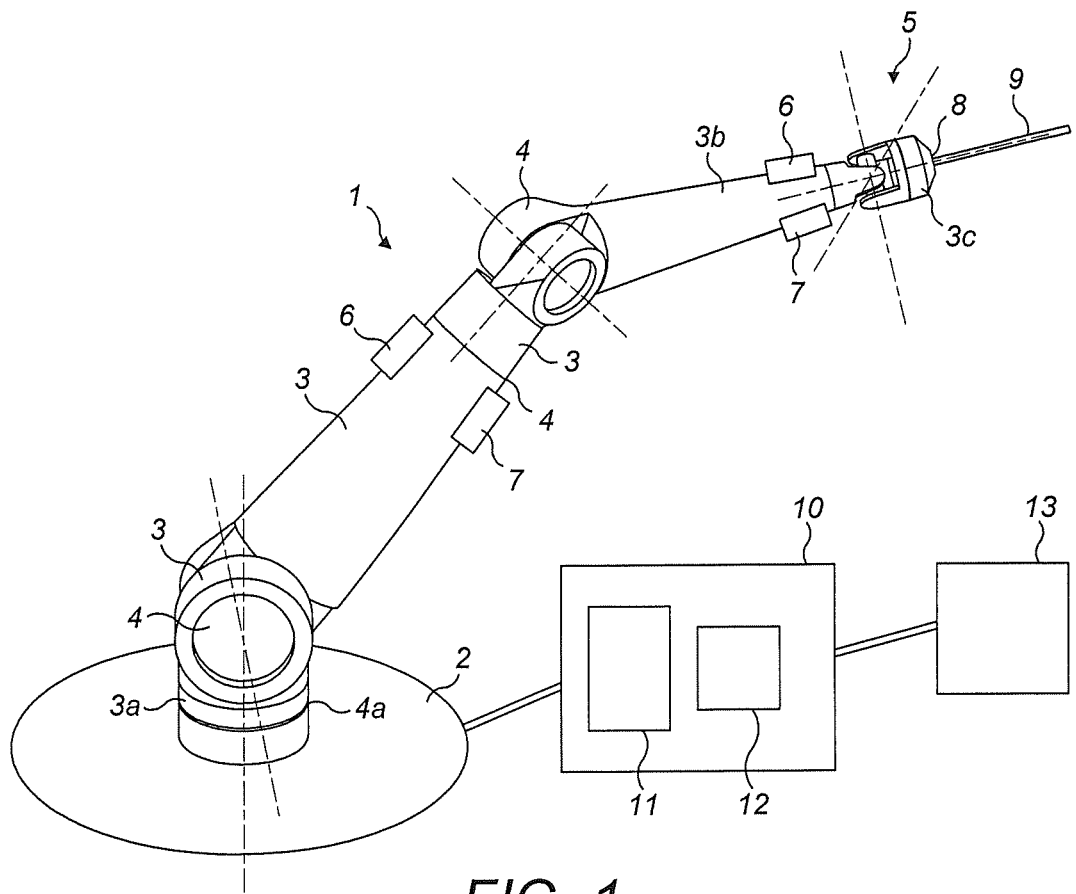
FIG. 1 shows a general representation of a surgical robot arm.

FIG. 1 shows a surgical robot having an arm 1 which extends from a base 2. The arm comprises a number of rigid arm segments, or limbs 3. The limbs are coupled by revolute joints 4. The most proximal limb 3a is coupled to the base by joint 4a. It and the other limbs are coupled in series by further ones of the joints 4. A wrist 5 is made up of four individual revolute joints. The wrist 5 couples one limb (3b) to the most distal limb (3c) of the arm. The most distal limb 3c carries an attachment 8 for a surgical instrument or tool 9. Limb 3b may be referred to as the 'forearm'. Each joint 4 of the arm has one or more motors 6 which can be operated to cause rotational motion at the respective joint, and one or more position and/or torque sensors 7 which provide information regarding the current configuration and/or load at that joint. For clarity, only some of the motors and sensors are shown in FIG. 1. The attachment point 8 for a tool can suitably comprise any one or more of: (i) a formation permitting a tool to be mechanically attached to the arm, (ii) an interface for communicating electrical and/or optical power and/or data to and/or from the tool, and (iii) a mechanical drive for driving motion of a part of a tool. In general, it is preferred that the motors are arranged proximally of the joints whose motion they drive, so as to improve weight distribution. Controllers for the motors, torque sensors and encoders may be distributed with the arm. The controllers are connected via a communication bus to control unit 10.

A control unit 10 comprises a processor 11 and a memory 12. Memory 12 stores in a non-transient way software that is executable by the processor to control the operation of the motors 6 to cause the arm 1 to operate in the manner described herein. In particular, the software can control the processor 11 to cause the motors (for example via distributed controllers) to drive in dependence on inputs from the sensors 7 and from a surgeon command interface 13. The control unit 10 is coupled to the motors 6 for driving them in accordance with outputs generated by execution of the software. The control unit 10 is coupled to the sensors 7 for receiving sensed input from the sensors, and to the command interface 13 for receiving input from it. The respective couplings may, for example, each be electrical or optical cables, or may be provided by a wireless connection. The command interface 13 comprises one or more input devices whereby a user can request motion of the arm in a desired way. The input devices could, for example, be manually operable mechanical input devices such as control handles or joysticks, or contactless input devices such as optical gesture sensors. The software stored in memory 12 is configured to respond to those inputs and cause the joints of the arm to move accordingly, in compliance with a predetermined control strategy. The control strategy may include safety features which moderate the motion of the arm in response to command inputs. Thus, in summary, a surgeon at the command interface 13 can control the robot arm 1 to move in such a way as to perform a desired surgical procedure. The control unit 10 and/or the command interface 13 may be remote from the arm 1.

Figure 2:
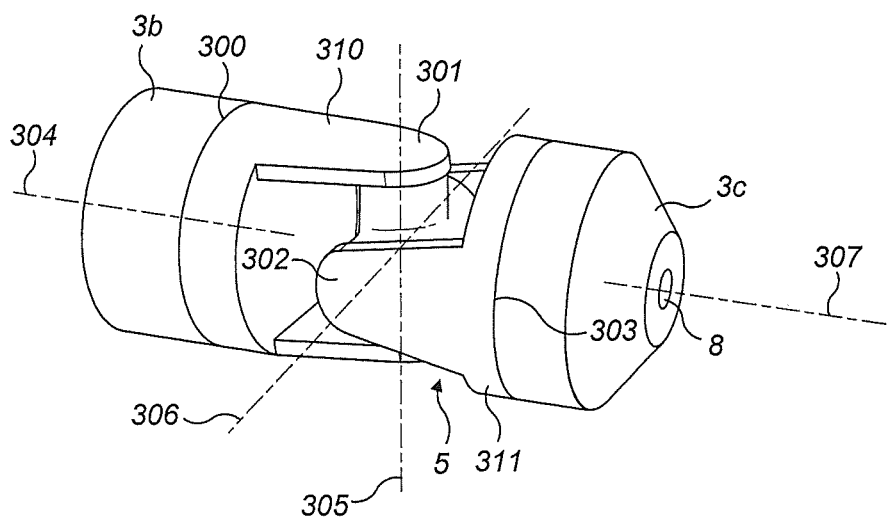
FIG. 2 shows in more detail the wrist of the surgical robot arm.

FIG. 2 shows the wrist 5 of the robot in more detail. The wrist comprises four revolute wrist joints 300, 301, 302, 303 and arm segments 310 and 311. The joints are arranged in series, with a rigid part of the arm extending from each joint to the next. The most proximal joint 300 of the wrist joins arm segment 3b to arm segment 310. Joint 300 has a "roll" rotation axis 304, which is directed generally along the extent of the limb 3b of the arm that is immediately proximal of the articulations of the wrist. The next most distal joint 301 of the wrist joins arm segment 310 to arm segment 311. Joint 301 has a "pitch" rotation axis 305 which is perpendicular to axis 304 in all configurations of joints 300 and 301. The next most distal joint 302 of the wrist joins arm part 310 to arm part 311. Joint 302 has a "yaw" rotation axis 306. Axes 305 and 306 are in general non-parallel rotation axes in all configurations of the joints 301 and 302. In this example, axes 305 and 306 are perpendicular to each other in all configurations of joints 301 and 302. In some configurations of the wrist, axis 306 is also perpendicular to axis 304. The next most distal joint of the wrist 303 joins arm segment 311 to arm segment 3c. Arm segment 3c is therefore located on the opposite side of the arm segment 311 than the joints 301 and 302. Joint 303 has a "roll" rotation axis 307 which is perpendicular to axis 306 in all configurations of joints 302 and 303. In some configurations of the wrist, axis 307 is also perpendicular to axis 305 and parallel with (and preferably collinear with) axis 304. There may be no other joints connecting arm segment 3c to arm segment 311. Thus arm segment 3c (and hence the tool attachment point 8) may be fast with the arm segment 311 about the axes 305 and 306 such that there is no relative motion between arm segment 311 and attachment point 8 about these axes.

It is preferable for axes 305 and 306 to intersect each other, since this gives a particularly compact configuration. Joints 300 and 303 may be positioned so that axes 304 and 307 can pass through the intersection of axes 305, 306 for some configurations of the wrist.

This design of wrist is advantageous in that it allows a wide range of movement from a tool attached to the attachment point 8 at the distal end of arm segment 3c, but with the wrist being capable of being assembled in a relatively compact form and without there being singularities at certain parts of the range of motion that could demand excessively high rates of motion at individual joints.

Various views of an example joint mechanism for implementing wrist 5 are shown in FIGS. 3 to 6. FIGS. 3 to 6 focus on the mechanism associated with joints 301 and 302 in FIG.

Figure 3:
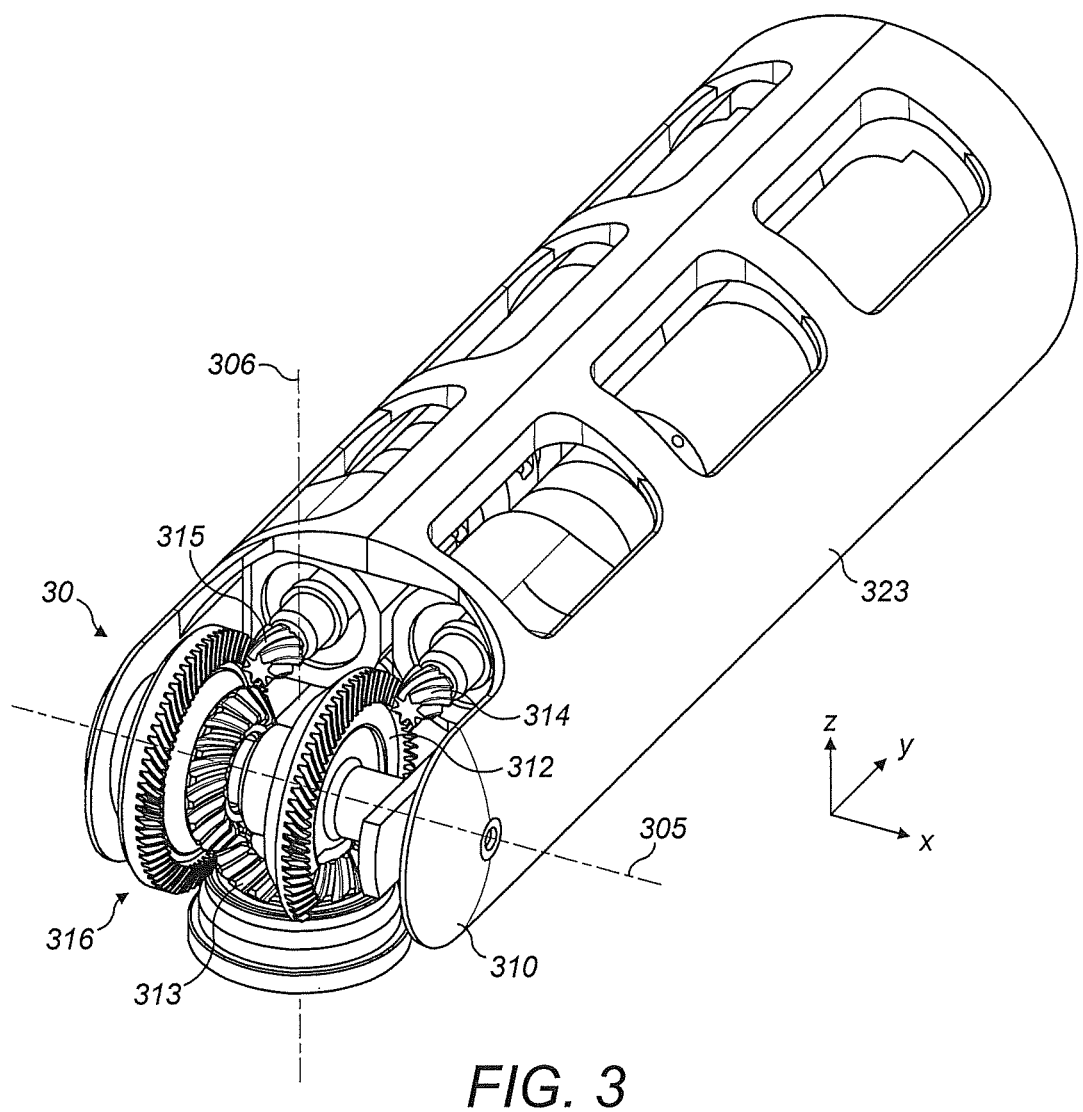
FIG. 3 shows part of a joint mechanism of the wrist from a distal position and one side.
Figure 4:
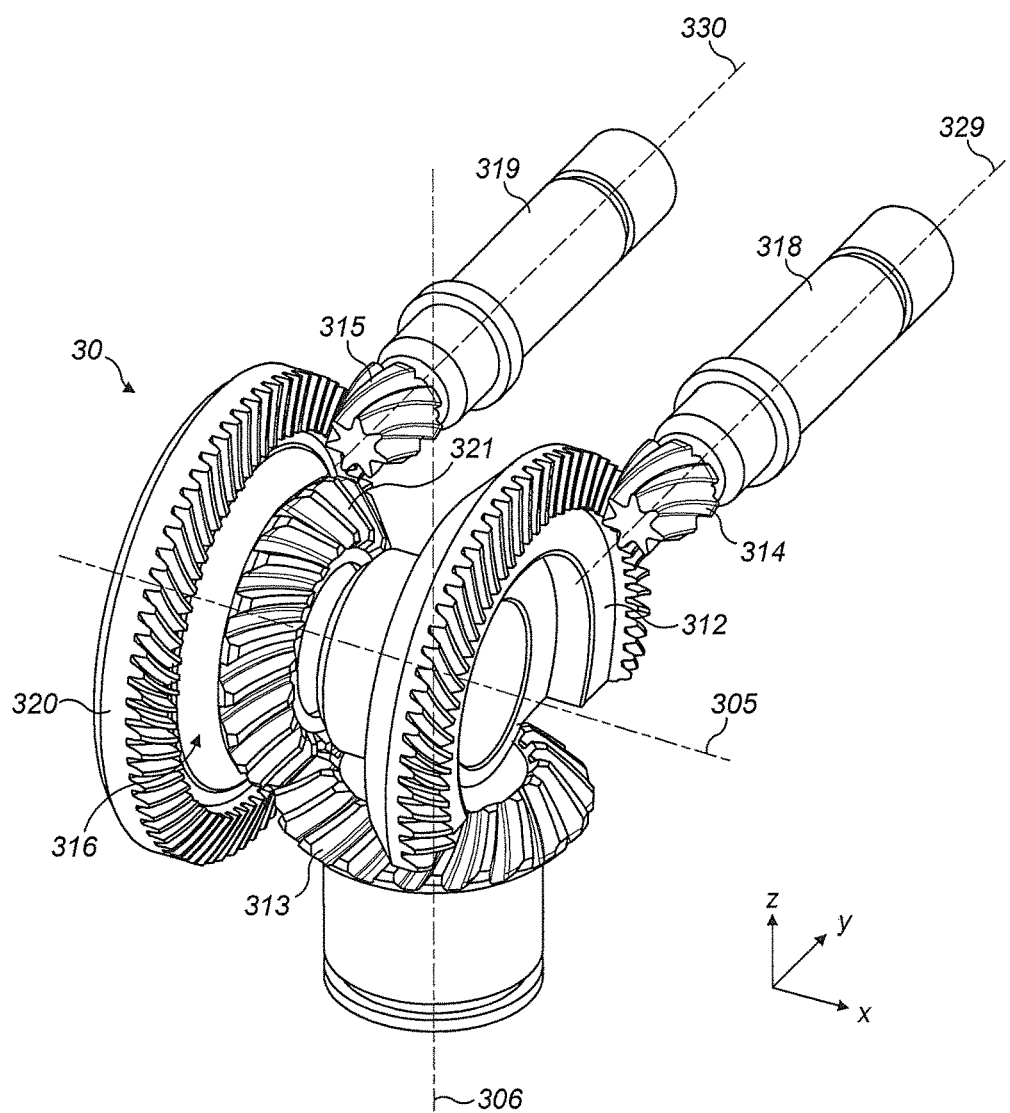
FIG. 4 shows an enlarged view of the joint mechanism with remaining parts of the robot arm omitted for clarity.
Figure 5A:
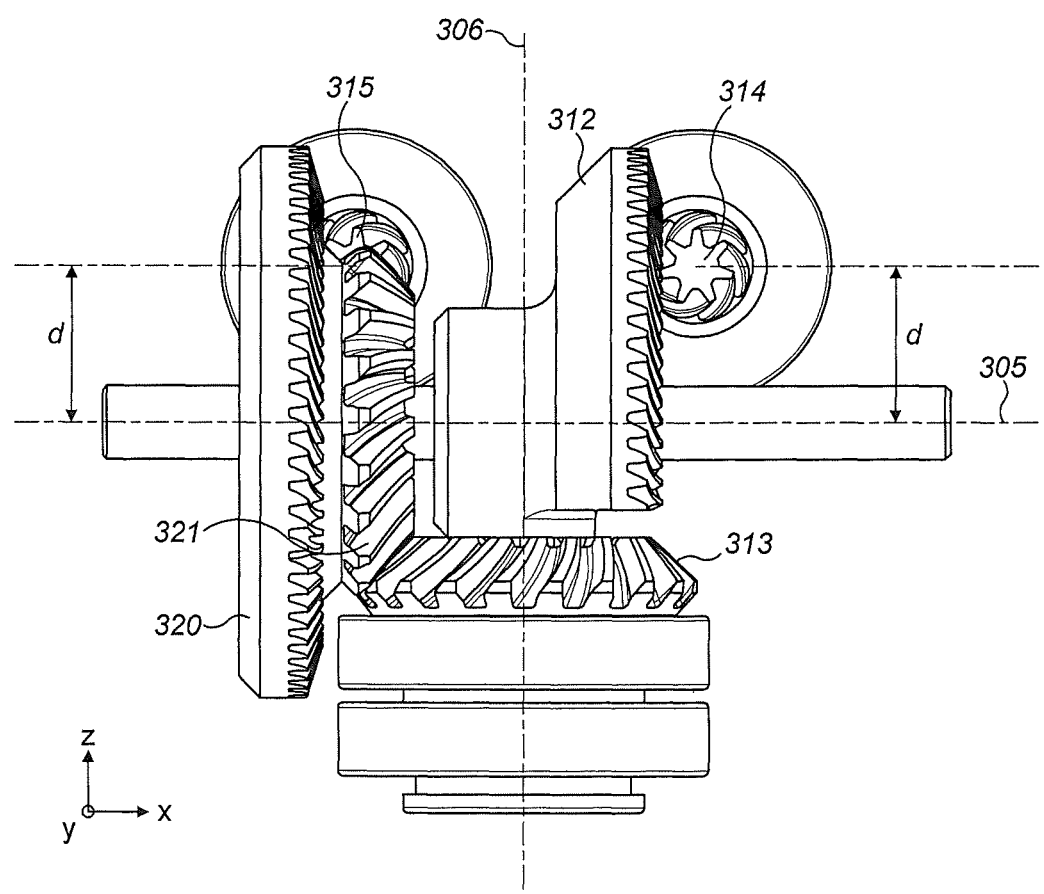
FIGS. 5A-5C shows various two-dimensional views of the joint mechanism.
Figure 5B:
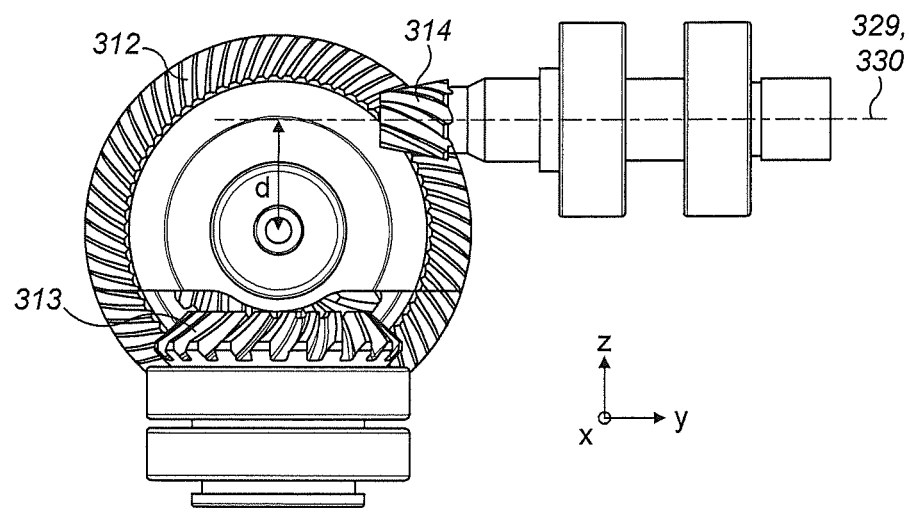
Figure 5C:
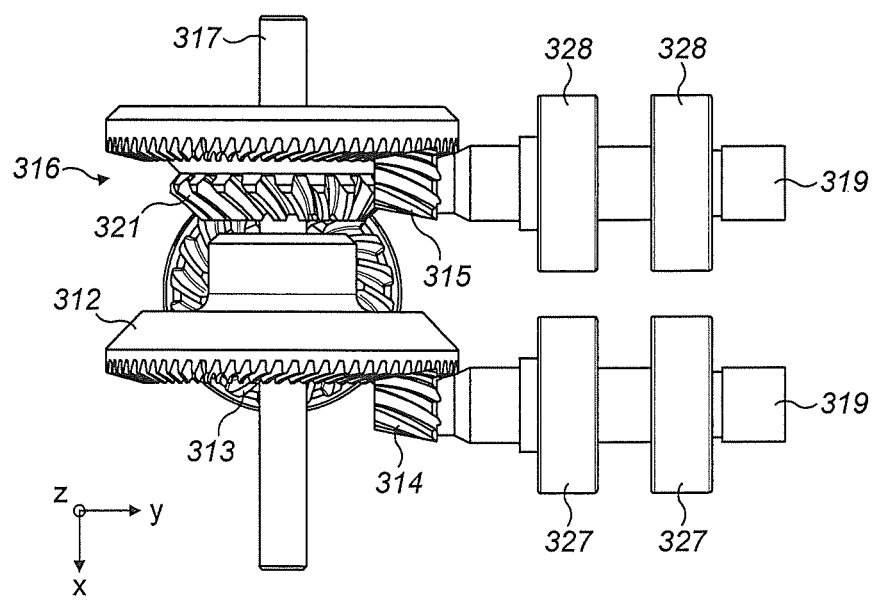
Figure 6:
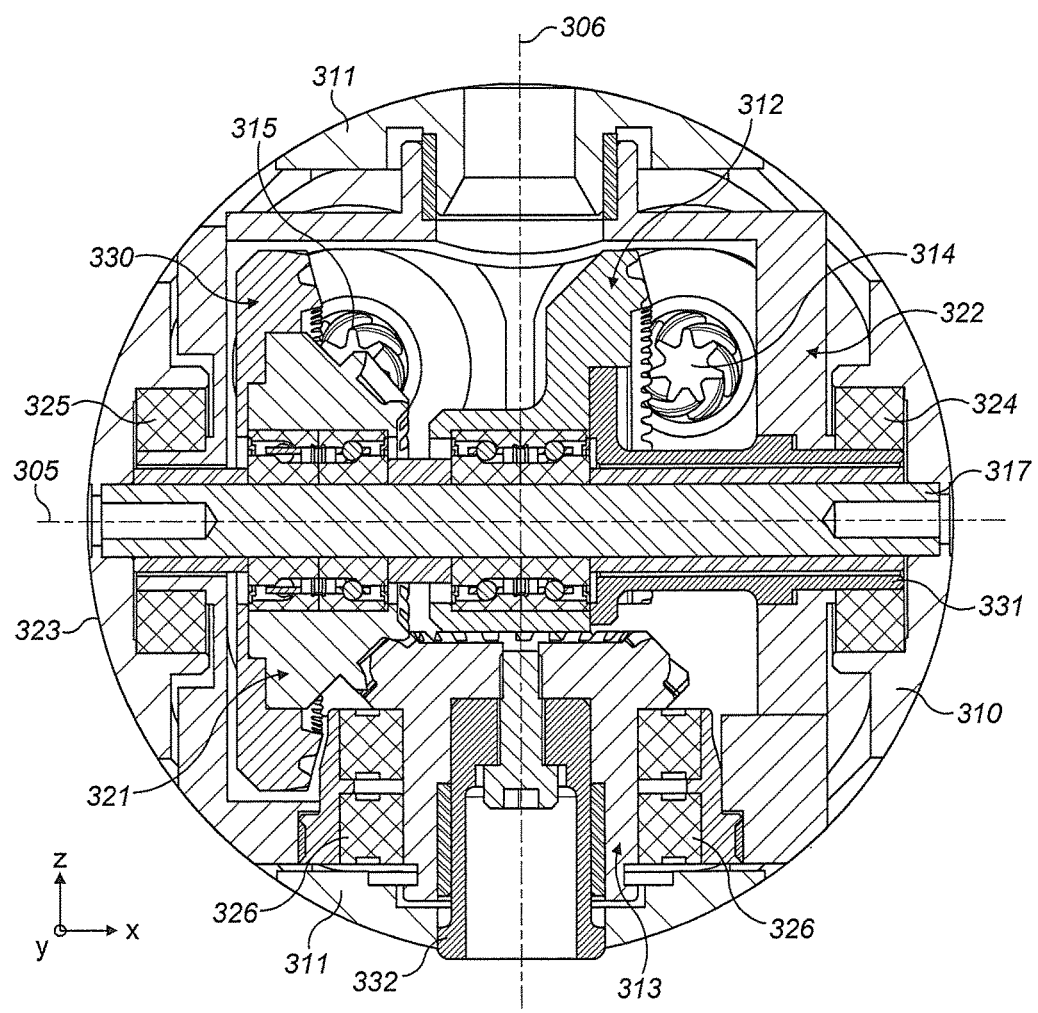
FIG. 6 shows the joint mechanism in section on a longitudinal plane in the proximal direction.

2. FIG. 3 shows the joint mechanism with respect to the first arm segment 310 with the second arm segment 311 omitted for clarity. FIG. 4 shows an enlarged view of the joint mechanism with the arm segments 310 and 311 omitted for clarity. FIGS. 5A-5C shows various two-dimensional views of the joint mechanism, and FIG. 6 shows a cross section view of the distal end of arm segment 310 in a plane transverse to the length of the segment 310.

Referring first to FIGS. 3 and 4, the joint mechanism is indicated generally at 30. The joint mechanism 30 is arranged to enable arm segment 310 to be articulated with respect arm segment 311 (omitted in these figures for clarity) about the non-parallel rotation axes 305 and 306. The arm segment 310 has an outer casing 323. The outer casing may be rigid, and defines an outer surface of the arm segment 310. The outer casing 323 defines an interior volume in which components of the robot arm, such as motors, sensors (e.g. position and/or torque sensors), cables and other components may be housed. Arm segment 311 also comprises an outer casing similarly defining an interior volume for housing components of the arm, but this has been omitted from FIG. 3 for clarity.

The arm segments 310 and 311 (including their associated outer casings) are moveable with respect to each other about the axes 305 and 306. Axes 305 and 306 are in general non-parallel axes. In this example, axes 305 and 306 are perpendicular to each other and additionally intersect.

The joint mechanism 30 comprises a first driven gear 312, a second driven gear 313, a first drive gear 314 and a second drive gear 315. The first and second drive gears 314 and 315 may alternatively be referred to as input gears, and the first and second driven gears 312 and 313 may alternatively be referred to as output gears. The joint mechanism additionally comprises an intermediary gear arrangement—indicated generally at 316—that couples the second drive gear 315 to the second driven gear 313.

Referring to FIG. 6, it can be seen that the first driven gear is coupled to the first arm segment 310 via a carrier 322. The carrier 322 is disposed about, or mounted on, an axle 317. Axle 317 is coincident with the rotation axis 305. Axle 317 is mounted to, and thus fast with, the arm segment 310. The carrier 322 is mounted to the arm segment 310 via laterally spaced bearings 324 and 325 that permit relative rotation of the carrier 322 relative to the arm segment 310 about the axle 317 (and thus axis 305), thus defining revolute joint 301. The first driven gear 312 is fast with the carrier 322. That is to say, the gear 312 and carrier 322 are fixed with respect to each other. The gear 312 is fixedly mounted to the carrier 322. The gear 312 may abut the carrier 322. That is, the carrier 322 may touch, or interface with, the gear 312. In other examples the carrier 322 may be fast with gear 312 but physically separated by one or more intermediary components such as spacers, washers etc. In this particular example the gear 312 is coupled to the carrier 322 via a torque sensor 331 that measures an applied torque about axis 305.

Carrier 322 also supports the second driven gear 313. Carrier 322 is coupled to the second driven gear 313 via bearings 326 to permit relative rotation of the carrier 322 and gear 313 about the rotation axis 306. Gear 313 is otherwise fast with carrier 322, and in particular fast about the rotation axis 305 such that there is no relative rotation or motion between gear 313 and carrier 322 about axis 305. The coupling of carrier 322 to the second driven gear 313 via bearings 326 defines the revolute joint 302. Gear 313 is fast with the arm segment 311.

Due to the function of the carrier 322 supporting the first driven gear and second driven gear, carrier 322 may alternatively be referred to as a chassis, or hub.

The arm may (as shown) further comprise torque sensors 331 and 332 for measuring torque about the joints 301 and 302. Torque sensor 331 measures the torque about the rotation axis 305 and torque sensor 332 measures the torque about the rotation axis 306. The sensors are housed within the interior volume defined by the outer casing 323. Both sensors comprise tubular components in the form of a sleeve. Torque sensor 331 sits around the axle 317 and torque sensor 332 sits around, i.e. is disposed about, axis 306. Both sensors 331 and 332 may be coupled to the control unit 10 and be configured to provide sensed torque readings to the control unit.

Referring back now to FIG. 4, the structure of the joint mechanism will be described in more detail.

The first driven gear 312 is a ring gear, or crown wheel. It is additionally formed as a sector; that is to say the arc defined by its teeth is less than 360 degrees. The sector has an operative arc, that is, a range of rotational motion through which it can be driven, that is less than 360 degrees. The arc of teeth of the sector may be greater than its operative arc. This is because the pinion 314 is not in point contact with gear 312 but instead engages a subset of its teeth in order to drive it. Thus the pinion 314 cannot drive the gear 312 through a range of motion equal to the arc of its teeth.

The gear 312 is disposed, or arranged, about the rotation axis 305. The gear 312 therefore has as its rotation axis the axis 305. Specifically, the first driven gear 312 is rotatably mounted on axle 317 (more clearly seen in FIGS. 5A and 5C) such that it can rotate with respect to the arm segment 310 about axis 305.

Driven gear 312 is engaged by the first drive gear 314, which in this example is a pinion. The term 'engage', as used herein when applied to a pair of gears, means that the teeth of one gear mesh, or interface, with the teeth of the other gear.

Pinion 314 is affixed to a first drive shaft 318 which is driven by a first electric motor mounted in the arm segment 310 (not shown). The drive shaft 318 is mounted in the arm segment 310 by bearings 327 to permit the shaft to rotate about its longitudinal axis 329 relative to the arm segment 310 (shown most clearly in FIG. 5C). The drive shaft 318 extends along the arm segment 310 and is attached at its (distal) terminal end to the pinion 314. The pinion 314 may be fast with the drive shaft 318. The drive shaft 318 extends in a direction perpendicular to the rotation axis 305 in all configurations of the joints 301 and 302. In other words, the longitudinal axis 329 of the drive shaft is perpendicular to the rotation axis 305 in all configurations of the joints 301 and 302.

Drive gear 314 drives rotation of the driven gear 312 about axis 305, as will be described in more detail below.

The axis of rotation of the first drive gear 314 (axis 329) and the first driven gear 312 (axis 305) are non-parallel (in particular, they are perpendicular to each other) and non-intersecting, as shown most clearly in FIGS. 5A and 5B. The first driven gear 312 is therefore a skew gear. In this particular example, the first driven gear 312 is a hypoid gear and drive gear 314 a hypoid pinion. Together they may be referred to as a hypoid gear set. The skew offset, that is the perpendicular distance between axes 329 and 305, is denoted d.

The second driven gear 313 is a bevel gear arranged about axis 306. It is disposed about the rotation axis 306 and arranged to undergo rotation about this axis relative to the first arm segment 310 and the first driven gear 312. The second driven gear 313 is fast with the arm segment 311. The second driven gear 313 may be mounted to the arm segment 311. The driven gear 313 and arm segment 311 may be arranged so that the gear 313 abuts the arm segment 311. The second driven gear 313 is also fast with the first driven gear 312 about the rotation axis 305. That is, gears 312 and 313 cannot undergo relative rotation or motion about axis 305. Put another way, gears 312 and 313 may be fast with each other except that gear 313 can rotate relative to gear 312 about axis 306. This means that a rotation of the first driven gear 312 about axis 305 causes a corresponding rotation of the second driven gear 313 about the axis 305.

The second driven gear 313 is fast with the first driven gear 312 about the rotation axis 305 by virtue of those gears' couplings to the carrier 322 (shown in FIG. 6). This is because: i) the first driven gear 312 is fast with the carrier 322; and ii) the second driven gear 313 is mounted to the carrier 322 via bearings 326 to permit relative rotation of the gear 313 and carrier about the rotation axis 306 but is otherwise fast with the carrier. The second driven gear 313 is therefore fast with the first driven gear 312 about the rotation axis 305.

In an alternative arrangement, the second driven gear 313 may be secured, or mounted, to the first driven gear 312 via bearings to permit relative rotation of the two driven gears about rotation axis 306. Such an arrangement would enable the two driven gears to be fast with each other about axis 305 without the second driven gear 313 being mounted to the carrier 322.

Because the first driven gear 312 is of part-circular form, the second driven gear 313 may be located in such a way that it intersects a circle coincident with gear 312 about axis 305 and having a radius equal to the outermost part of gear 312. This is most clearly shown in FIGS. 5A and 5B. This arrangement is particularly useful for reducing the size of the joint mechanism.

The second driven gear 313 is driven by the second driving gear 315 to rotate about the axis 306. In this example the second driving gear 315 is a pinion. The pinion is fast with a second drive shaft 319 which is driven by a second electric motor mounted in the arm segment 310 (not shown). The second drive shaft 319 extends along the length of the arm segment 310 and is attached at its distal terminal end to the driving gear 315. Drive shaft 319 is mounted in the arm segment 310 by bearings 328 that permit the shaft to rotate about its longitudinal axis 330 relative to the arm segment 310.

The drive shaft 319, and hence its longitudinal axis 330, extends in a direction perpendicular to the rotation axis 305 in all configurations of the joints 301 and 302. Drive shaft 319 is therefore parallel to drive shaft 318. Drive shaft 319 is also symmetrical with drive shaft 318 about a first plane that contains the rotation axis 306 and is perpendicular to axis 305 (most clearly seen in FIG. 5A). The first plane therefore contains the rotation axis 306 and the centreline of arm segment 310. It can further be seen from FIG. 5A that both drive shafts 318 and 319 lie on the same side of a second plane containing the axle 317 (and rotation axis 305). That second plane is parallel to the longitudinal direction, or axis, of the arm part 310. Thus, the second plane is parallel to the longitudinal axes 329 and 330 of the drive shafts 318 and 319 respectively. The second plane is perpendicular to the axis 306 in at least one configuration of the joints 301 and 302. In the arrangement shown, that configuration is when the longitudinal axis of arm part 310 is parallel to the longitudinal axis of arm part 311 (i.e. when arm part 311 is in not in pitch or yaw relative to arm part 310).

In the arrangement shown, drive gears 314 and 315 also lie on the same side of a third plane that contains axis 305 and is perpendicular to the longitudinal axis of the arm part 310 (most clearly shown in FIGS. 5B and 5C). The third plane contains both axes 305 and 306 in at least one configuration of the joints 301 and 302. That configuration is when the longitudinal axis of arm part 310 is parallel to the longitudinal axis of arm part 311 (i.e. when arm part 311 is in not in pitch or yaw relative to arm part 310).

The second drive gear 315 and second driven gear 313 are coupled by the intermediary gear arrangement 316 to transfer rotation of the drive gear 315 to the driven gear 313. Specifically, the intermediary gear arrangement 316 engages both the drive gear 315 and the driven gear 313. The intermediary gear arrangement in this example comprises a first intermediate gear 320 that engages the drive gear 315, and a second intermediate gear 321 that engages the driven gear 313. The first and second intermediate gears are fast with each other. As is more clearly shown in FIGS. 5A and 5C, the intermediate gears 320 and 321 are fixed, or mounted, to each other. In particular, gear 320 abuts gear 321.

The first intermediate gear 320 is a ring gear, or crown wheel. The second intermediate gear 321 is a bevel gear. Both gears are rotatably mounted on the same axle 317 as the first driven gear 312 and so are arranged around axis 305. Thus the intermediary gear arrangement 316 is disposed about the axis 305; i.e. the intermediary gear arrangement has as its rotation axis the axis 305. The Intermediary gear arrangement 316 is rotatable about axle 317 such that it can undergo relative rotation with respect to the arm segment 310 about axis 305. As can be seen in FIG. 5A, the intermediary gear arrangement 316 and the first driven gear 312 are located on the axle 317 such that they are on opposite sides of the rotation axis 306. The intermediary gear arrangement 316 and first driven gear 312 are therefore on opposite sides of the plane that contains axis 306 and is perpendicular to axis 305. Thus the intermediary gear arrangement is located on a single side of the first driven gear 312 in a direction along the rotation axis 305.

The axis of rotation of the second drive gear 315 (axis 330) and the axis of rotation of intermediate gear 320 (axis 305) are non-parallel and non-intersecting. Thus the first intermediate gear 320, like the first driven gear 312, is a skew gear. In this example, the first intermediate gear 320 is a hypoid gear, and the drive gear 315 a hypoid pinion. The drive gear 315 and first intermediate gear 320 therefore form a hypoid gear set.

The first intermediate gear 320 and first driven gear 312 have the same radius and tooth density (i.e. number of teeth per unit circumference). They may also have the same tooth profile. Though in this arrangement gears 320 and 312 have different widths when viewed in cross-section (as shown in FIGS. 5A and 5C), in other arrangements gears 320 and 312 may be identical with the exception that gear 312 is a sector. The first intermediate gear 320 and first driven gear 312 also have an equal skew offset; i.e. the offset d between the axis of rotation 329 of drive gear 314 and axis of rotation 305 of driven gear 312 is equal to the offset d between the axis of rotation 330 of drive gear 315 and axis of rotation 305 of gear 320. This is most clearly shown in FIGS. 5A and 5B. Gears 312 and 320 are therefore identical hypoid gears, with the exception that gear 312 is a sector. Similarly, drive gear 314 is identical to drive gear 315.

The second intermediate gear 321 and second driven gear 313 have equal numbers of teeth and a drive ratio of 1:1. Gears 321 and 313 are therefore mitre gears. The mitre gears could be straight toothed or spiral toothed.

The operation of the joint mechanism 30 will now be described.

To drive motion about axis 305, the first motor is operated to drive the drive shaft 318 to rotate relative to the arm segment 310 about its longitudinal axis 329. Rotation of the drive shaft 318 causes the driven gear 314 to rotate about the axis 329. Because the teeth of the drive gear 314 are meshed with the teeth of the driven gear 312, rotation of the drive gear 314 drives the driven gear 312 to rotate about its axis of rotation 305 relative to the arm segment 310. This drives a rotation of the second driven gear 313 (and hence the arm segment 311) about the axis 305 relative to the arm segment 310 via joint 301. Referring briefly to FIG. 6, it can be seen how rotation of the first driven gear 312 about axis 305 causes rotation of carrier 322 (which is fast with gear 312) about that axis. This in turn causes the second driven gear 313 (which is fast with the carrier 312 about axis 305) to also rotate about axis 305.

The first driven gear 312 is capable of rotating about axis 305 in either angular direction. The direction of rotation about axis 305 is dependent on the direction of rotation of the drive gear 314. That is, rotation of drive gear 314 in a first direction about the longitudinal axis 329 of the drive shaft 318 causes rotation of the arm segment 311 relative to the arm segment 310 in a first direction about axis 305; and rotation of drive gear 314 about axis 329 in a second direction opposite the first direction causes rotation of the arm segment 311 relative to the arm segment 310 in a second direction about axis 305 opposite the first direction.

It will be noted that rotation of the second driven gear 313 about axis 305 whilst the drive shaft 319 remains stationary will also cause the second driven gear 313 to rotate relative to the first driven gear 312 (and hence also the carrier 322 and arm segment 310) about axis 306, causing parasitic motion of the arm segment 311 relative to arm segment 310 about axis 306. When isolated rotation about axis 305 is desired, control system 10 may operate to drive the drive shaft 319 in tandem with drive shaft 318 to isolate rotation about axis 305 from rotation about axis 306. In the arrangement shown, drive shaft 319 is driven in the same angular direction as drive shaft 318 to isolate rotation about the axis 305. The control system 10 may therefore be configured to cause drive shaft 319 to be driven when drive shaft 318 is driven in such a way as to prevent gear 313 from rotating relative to gear 312 about the rotation axis 306.

To drive motion about axis 306, the second motor is operated to drive the drive shaft 319 to rotate about its longitudinal axis 330 relative to the arm segment 310. Rotation of the drive shaft 319 causes the affixed second drive gear 315 to also rotate about axis 330 relative to the arm segment 310. The teeth of the second drive gear 315 mesh with the teeth of the first intermediate gear 320 and so rotation of the second drive gear 315 drives the rotation of the first intermediate gear about its axis of rotation 305. The first intermediate gear 320 is fast with the second intermediate gear 321 and so rotation of the second drive gear 315 also causes rotation of the second intermediate gear 321 about its axis of rotation 305. The second intermediate gear 321 engages the second driven gear 313 and so rotation of gear 321 drives rotation of the gear 313 about its axis of rotation 306. Thus the second intermediate gear 321 and the second driven 313 gear (which in this example form a pair of mitre gears) operate to transfer rotation of the intermediary gear arrangement about its axis of rotation 305 to rotation of the second driven gear about axis 306. The intermediary gear arrangement 316 thus operates to transfer rotation of the second drive gear 315 about the longitudinal axis 330 of its affixed drive shaft 319 to rotation about the non-intersecting axis 306.

The intermediary gear arrangement 316 is capable of rotating about axis 305 in either angular direction, and the second driven gear 313 is capable of rotating about axis 306 in either angular direction. The direction of rotation of the intermediary gear arrangement 316 about axis 305—and thus the direction of rotation of the second driven gear 313 about axis 306—is dependent on the direction of rotation of the second drive gear 315 about the longitudinal axis 330 of the drive shaft 319. That is, rotation of the second drive gear 315 in a first direction about axis 330 causes rotation of the arm segment 311 relative to arm segment 310 in a first direction about axis 306; and rotation of the second drive gear 315 in a second direction about the axis 330 opposite the first direction causes rotation of the arm segment 311 relative to the arm segment 310 in a second direction about axis 306 opposite the first direction.

It is noted that the intermediary gear arrangement 316 is mounted on the same axle 317 as the first driven gear 312 but is not fast with it. For example, it can be seen in FIGS. 5A and 5C that the intermediary gear arrangement 316 and first driven gear 312 are laterally spaced on axle 317. Intermediary gear arrangement 316 and driven gear 312 are therefore capable of rotating with respect to each other about axis 305. This means that rotation of the drive shaft 319 (which causes the second driven gear 313 to rotate about axis 306) does not cause parasitic motion of gear 313 about axis 305. Thus the joint mechanism 30 permits isolated rotation of the second driven gear 313 (and hence arm segment 311) about axis 306 with respect to arm segment 310 without the need for compensatory motion of drive gear 318.

Joint mechanism 30 can also drive a compounded motion of arm segment 311 relative to arm segment 310 about both axes 305 and 306. One way to drive rotation about both axes concurrently is to drive the drive shaft 318 whilst keeping drive shaft 319 fixed, as described above. In certain circumstances the resultant rotation of the second driven gear 313 about axis 305 may be desirable and not parasitic. In other circumstances compound articulation of both joints 301 and 302 may be effected by driving both driving shafts 318 and 319 in tandem. The control unit 10 may independently control the rotation speed and direction of each drive shaft 318 and 319 by controlling their associated electric motors. In this way the control unit 10 can control the direction of rotation about each of axes 305 and 306 respectively and the ratio of the rotation speeds about axis 305 to 306 (or vice versa). The ratio of the rotation speeds about axes 305 and 306 may be dependent on the ratio of the rotation speeds of drive gears 314 and 315 respectively. For example, a higher rotation speed of the first drive gear 314 relative to the second drive gear 315 causes relatively larger amounts of rotation about axis 305 relative to axis 306 compared to a slower rotation speed of drive gear 314 relative to drive gear 315.

Various aspects of the example joint mechanism 30 described above may contribute to providing an advantageous mechanism for articulating one robot arm segment relative to another.

The mechanism 30 enables one robot arm segment to be articulated relative to another robot arm segment by a pair of joints having two non-parallel intersecting axes of rotation without requiring a universal joint in either arm segment to effect the motion. This enables the length of the arm segments to be reduced as they don't need to accommodate the universal joints or space for their motion during articulations. The avoidance of universal joints to effect motion may also lead to a smoother motion of the joints.

The mechanism can conveniently be arranged so that both drive gears 314 and 315 and their associated drive shafts 318 and 319 lie on one side of a plane containing axis 305 (as shown in FIG. 5). This provides an efficient packing arrangement within the outer casing 323 of the arm segment 310 by freeing up space within the interior volume of the outer casing to house other components of the robot arm, such as electronic cables, sensors etc.

The design of the intermediary gear arrangement 316 and the fact it has a single axis of rotation 305 enables it to be mounted on the same axle 317 as the first driven gear 312. The use of a single axle that is secured at both its terminal ends to support both the intermediary gear arrangement and first driven gear provides a stiff arrangement with potentially less bending of the axle. Reducing the bending of the axle may be helpful for improving the accuracy of the readings from the torque sensor 331 that measures torque about that axle.

Mounting both the intermediary gear arrangement 316 and first driven gear 312 on common axle 317 may also simplify the installation and/or maintenance of the torque sensor 332 by enabling the sensor to be slid into place from the outside of the joint.

The arrangement of the joint mechanism 30 enables a large number of similar components to be used. For example, the first driven gear 312 and first intermediate gear 320 may have an identical radius and tooth profile, meaning they could be manufactured using common equipment. This in turn means that drive gear 314 may have an equal tooth profile to drive gear 315, meaning they too could be manufactured using common equipment. The associated drive shafts 318 and 319 may also be identical. Additionally, the second intermediate gear 321 and second driven gear 313 may form a pair of mitre gears having an equal number of teeth and equal pitch and pressure angles. If the mitre gears are additionally straight-toothed, the gears 321 and 313 may be identical. The reduced number of mechanically distinct parts may reduce the design and manufacturing effort and cost of the mechanism.

Though the above disclosure has been made with reference to the specific example illustrated in FIGS. 3 to 6, it will be appreciated that various modifications to the joint mechanism may be made.

For example, in the above-described embodiments, the first driven gear 312 is a sector, but in other examples the first intermediate gear 320 may be a sector and the first driven gear 312 not a sector (that is, the first driven gear 312 could have an operative arc of 360 degrees). Alternatively, both the first driven gear 312 and first intermediate gear 320 may be sectors. Having both gears as sectors may be permissible in certain implementations where only reduced operating angles of the joints are required, and enables the joint mechanism to be of reduced weight and potentially of reduced size.

The operative arc of the sector may vary in dependence on the mechanical implementation of the joint mechanism 30. The operative arc may for example be less than 270°, or 180° or 90°, or 60°. In the specific implementation of the joint mechanism 30 shown in FIGS. 3 to 6 (i.e. within the wrist of the robot arm), it has been appreciated that the operative arc of the sector 312 may be reduced to 50° so that the mechanism provides ±25° of rotation about the axis 305. This is because the arrangement of the joints 300, 301, 302 and 303 (i.e. a pair of roll joints with a pitch and jaw joint between them) provides a degree of mechanical redundancy meaning a wide range of positions of the distal end of the robot arm can be achieved even with a restricted range of motion about axis 305. Reducing the operative arc of the sector 312 to 50° may lead to further reductions in the size and weight of the joint mechanism. For example, a rotational range of motion of ±25° may only require the sector to have teeth defining an arc spanning 90°.

The first driven gear 312 and first intermediate gear 320 are described as hypoid gears in the above examples. The use of hypoid gears allows for a relatively high torque capacity in a relatively compact form. However, these gears may in general be any suitable type of ring gear. For example, one or both of the first driven gear 312 and first intermediate gear 320 may be another type of skew-axis gear, such as a Spiroid® gear, or worm gear. It follows that one or both of the drive gears 314 and 315 may be Spiroid pinions or worms as appropriate. As another example, one or both of the first driven gear 312 and first intermediate gear 320 may be bevel gears such that the axis of rotation of the associated drive gear(s) 314 and 315 intersects the axis of rotation 305. The bevel gears may be straight-toothed or spiral-toothed.

The second intermediate gear 321 and the second driven gear 313 need not be mitre gears as in the above examples, but could in general be bevel gears. That is, the drive ratio of the gears 321 and 313 need not be 1:1 and the gears need not have equal numbers of teeth.

The intermediate gear arrangement 316 and the first driven gear have been described as being mounted on a common axle 317. In an alternative arrangement the intermediate gear arrangement 316 and the first driven gear 312 could be mounted on respective cantilevered axles. Such an arrangement may be useful to provide a volume between the gear arrangement and driven gear that may be used to house other components of the robot arm, such as sensors, electronics etc.

In the illustrative examples described above, the joint mechanism 30 is arranged so that the two rotation axes 305 and 306 are orthogonal. However, the axes 305 and 306 need not be orthogonal and are in general two non-parallel intersecting axes. They may be substantially orthogonal to each other. The angle between axes 305 and 306 may be set by the arrangement of the second intermediate gear 321 and the second driven gear 313. That is, the second driven gear 313 and second intermediate gear 321 may be arranged so that the axis of rotation of the second driven gear 313 (axis 306) is non-perpendicular to the axis of rotation of the second intermediate gear 321 (axis 305). In addition, axis 305 need not be perpendicular to the longitudinal direction of arm part 310. For example, the joint mechanism may be arranged so that the axis 305 is canted with respect to the longitudinal axis of the arm segment 310.

The intermediary gear arrangement 316 has been described as comprising two intermediate gears 320 and 321. However, the intermediary gear arrangement may comprise only one gear disposed about axis 305. For example, the intermediary gear arrangement 316 may comprise a single bevel gear that engages both drive gear 315 and the second driven gear 313. Alternatively, the intermediary gear arrangement may comprise three or more intermediate gears each disposed about the axis 305. A first of the intermediate gears may engage the drive gear 315 and a second of the intermediate gears may engage the driven gear 313. The remaining intermediate gears may be used to drive further components of the robot arm or form part of a gearbox transmission between the drive gear 315 and driven gear 313.

The joint mechanism has been described as being implemented in a wrist of a robotic arm. However, it will be appreciated that the mechanism can be implemented in any suitable joint coupling one arm segment of the robot arm to another arm segment of the robot arm. The joint could be another joint at a more proximal end of the robot arm, such as an elbow joint or some other joint at the proximal end of the kinematic chain. Further, the joint mechanism need not be implemented in a surgical robot, but could be implemented in other types of robot, such as an industrial robot.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present disclosure may consist of any such individual feature or combination of features. In view of the foregoing description it will be evident to a person skilled in the art that various modifications may be made within the scope of the disclosure.

The invention claimed is:

1. A robot arm comprising a first arm segment and a second arm segment coupled to each other by a first revolute joint having a first rotation axis and a second revolute joint having a second rotation axis non-parallel to the first rotation axis, and a joint mechanism configured to articulate the first arm segment relative to the second arm segment about the first and second rotation axes, the joint mechanism comprising:
    a first driven gear disposed about an axle coincident with the first rotation axis;
    a second driven gear disposed about the second rotation axis and fast with a second arm segment of the robot arm;
    a first drive gear disposed about a third rotation axis and configured to drive the first driven gear to rotate about the first rotation axis, the first drive gear being arranged to engage the first driven gear;
    a second drive gear configured to drive the second driven gear to rotate about the second rotation axis;
    an intermediary gear arrangement arranged to engage the second drive gear and the second driven gear, whereby rotation of the intermediary gear arrangement relative to the first arm segment can be driven, the intermediary gear arrangement comprising a first intermediate gear arranged to engage the second drive gear, and a second intermediate gear arranged to engage the second driven gear, the second intermediate gear intersecting a projection of a profile of the second drive gear in the direction of the longitudinal axis of the second drive gear; and
    wherein the third rotation axis and the first rotation axis are non-intersecting.

2. A robot arm as claimed in claim 1, wherein the first rotation axis is transverse to the second rotation axis.

3. A robot arm as claimed in claim 1, wherein the first rotation axis intersects the second rotation axis.

4. A robot arm as claimed in claim 1, wherein the first drive gear is attached to a first drive shaft extending along the first arm segment and/or the second drive gear is attached to a second drive shaft extending along the first arm segment.

5. A robot arm as claimed in claim 1, wherein the first drive gear is attached to a first drive shaft extending along the first arm segment and the second drive gear is attached to a second drive shaft extending along the first arm segment, and the first and second drive shafts lie on one side of a plane on which the axle lies.

6. A robot arm as claimed in claim 1, wherein the first driven gear is a ring gear.

7. A robot arm as claimed in claim 6, wherein the first driven gear is a hypoid gear.

8. A robot arm as claimed in claim 1, wherein the intermediary gear arrangement is mounted on the axle, the axle being mounted at each of its ends to the first arm segment.

9. A robot arm as claimed in claim 1, wherein the first intermediate gear is fast with the second intermediate gear.

10. A robot arm as claimed in claim 1, wherein the first driven gear is a sector.

11. A robot arm as claimed in claim 10, wherein an operative arc of the sector is less than or equal to 50 degrees.

12. A robot arm as claimed in claim 1, wherein the first intermediate gear is a ring gear.

13. A robot arm as claimed in claim 1, wherein the first intermediate gear is a hypoid gear.

14. A robot arm as claimed in claim 1, wherein the first drive gear and first driven gear form a first hypoid gear set, and the second drive gear and first intermediate gear form a second hypoid gear set, the first and second hypoid gear sets having an equal skew offset.

15. A robot arm as claimed in claim 1, wherein the second intermediate gear and the second driven gear are bevel gears.

16. A robot arm as claimed in claim 1, wherein the joint mechanism further comprises a carrier attached to the first arm segment by the first revolute joint and attached to the second arm segment by the second revolute joint, the carrier being fast with the first driven gear.

17. A robot arm as claimed in claim 1, wherein the first and second revolute joints are wrist joints of the robotic arm.

18. A robot arm as claimed in claim 1, wherein the robot arm is a surgical robot arm, and the robot arm comprises a tool or tool attachment fast with the second arm segment about the first and second rotation axes.

19. A robot arm as claimed in claim 18, wherein the robot arm comprises a third arm segment adjacent the second arm segment and located on the opposite side of the second arm segment to the joint mechanism, and a third revolute joint that attaches the third arm segment to the second arm segment, wherein the third arm segment comprises a tool or a tool attachment.

20. A robot arm as claimed in claim 1, further comprising a control unit arranged to respond to command signals commanding motion of the robot arm by driving the first and second drive shafts to rotate, the control unit being configured to, when the robot arm is commanded to articulate about the first axis without articulating about the second axis, drive the first shaft to rotate to cause articulation about the first axis and also drive the second shaft to rotate in such a way as to negate parasitic articulation about the second axis.

* * * * *